United States Patent [19]

Tsuchida et al.

[11] 4,407,952

[45] Oct. 4, 1983

[54] METHOD FOR PRODUCING L-PHENYLALANINE BY FERMENTATION

[75] Inventors: Takayasu Tsuchida, Kawasaki, Japan; Konosuke Sano, Madison, Wis.

[73] Assignee: Ajinomoto Company Incorporated, Tokyo, Japan

[21] Appl. No.: 159,477

[22] Filed: Jun. 16, 1980

[30] Foreign Application Priority Data

Jun. 15, 1979 [JP] Japan .................................. 75483

[51] Int. Cl.³ .................... C12N 15/00; C12P 13/22; C12R 1/19
[52] U.S. Cl. .................................. 435/108; 435/172; 435/849; 435/317
[58] Field of Search ............ 435/108, 172, 317, 849, 435/848

[56] References Cited

U.S. PATENT DOCUMENTS

| | | | |
|---|---|---|---|
| 3,660,235 | 5/1972 | Okumura et al. | 435/108 |
| 3,759,790 | 9/1973 | Nakayama et al. | 435/108 |
| 3,909,353 | 9/1975 | Tsuchida et al. | 435/108 |
| 3,917,511 | 11/1975 | Nakayama et al. | 435/108 |
| 4,237,224 | 12/1980 | Cohen et al. | 435/172 X |
| 4,278,765 | 7/1981 | Debabov et al. | 435/172 |

Primary Examiner—Esther M. Kepplinger
Attorney, Agent, or Firm—Oblon, Fisher, Spivak, McClelland & Maier

[57] ABSTRACT

L-phenylalanine is produced by fermentation by culturing in a culture medium an L-phenylalanine producing microorganism constructed by incorporating a hybrid plasmid in a recipient strain of the genus Escherichia and recovering the L-phenylalanine which accumulates in the culture medium, said hybrid plasmid containing a deoxyribonucleic acid fragment possessing genetic information related to L-phenylalanine production and obtained from a phenylalanine analogue resistant mutant of the genus Escherichia.

5 Claims, No Drawings

METHOD FOR PRODUCING L-PHENYLALANINE BY FERMENTATION

BACKGROUND OF THE INVENTION

1. Field of the Invention

The present invention relates to a method for producing L-phenylalanine for fermentation.

2. Description of the Prior Art

In the past L-phenylalanine has been produced by the fermentation of auxotrophic or drug-resistant mutants of the genera Brevibacterium, Corynebacterium and Escherichia as disclosed in U.S. Pat. Nos. 2,973,304 and 3,660,235. However, a need continues to exist for a method by which L-phenylalanine can be produced in greater yields.

SUMMARY OF THE INVENTION

Accordingly, an object of the present invention is to provide a method by which L-phenylalanine can be produced in greater quantities.

Briefly, this object and other objects of the present invention as hereinafter will become more readily apparent can be attained by a method producing L-phenylalanine by culturing an L-phenylalanine producing microorganism constructed by incorporating a hybrid plasmid in a recipient strain of the genus Escherichia in a culture medium, and recovering the L-phenylalanine which accumulates in the culture medium, said hybrid plasmid containing a deoxyribonucleic acid fragment possessing genetic information related to L-phenylalanine production and obtained from a phenylalanine-analogue resistant mutant of the genus Escherichia.

DETAILED DESCRIPTION OF THE PREFERRED EMBODIMENTS

In the microorganism preparation procedure of the present invention, a mutant of the genus Escherichia resistant to phenylalanine-analogue as the deoxyribonucleic acid (hereinafter referred to as DNA) donor can be chosen, and A DNA fragment possessing genetic information related to L-phenylalanine production is obtained from the mutant. The DNA fragment is then inserted into a plasmid obtained from *Escherichia coli*, and the resulting recombinant plasmid is introduced into a microorganism of the genus Escherichia.

Any known mutant of the genus Escherichia resistant to phenylalanine analogue can be used as the DNA donor. These mutants can be obtained by the usual artificial mutation techniques.

The phenylalanine analogues which can be used in the present invention normally inhibit the growth of microorganisms of the genus Escherichia. However, the inhibition is partly or completely suppressed by the presence of L-phenylalanine. Suitable examples of phenylalanine-analogues include o-, m-, and p-fluorophenylalanine, o-, m- and p-aminophenylalanine, β-phenylserine, cyclohexylalanine, α-amino-β-phenylethane sulfonic acid, o-, m- and p-chlorophenylalanine, o-, m- and p-bromophenylalanine, β-2-thienylalanine, β-3-thienylalanine, β-2-furylalanine, β-2-pyrolealanine, 1-cylopentene-1-alanine, 1-cyclohexen-1-alanine, 2-amino-4-methyl-4-hexenic acid, S-(1,2-dichlorovinyl)-cysteine, β-4-pyridylalanine, β-2-pyridylalanine, β-4-pyrazolealanine, and p-nitrophenylalanine.

The DNA-donor employed in the present invention also includes mutants which are resistant to tryptophan-analogues such as 5-fluoro-tryptophan, and are resistant to 2-thienylalanine or require tyrosine for growth besides resistance to phenylalanine analogues.

Chromosomal DNA is extracted from the mutant in the usual manner and treated with a restriction endonuclease by the usual method.

The plasmid or phage DNA used as the vector in the synthesis procedure is also treated with a restriction endonuclease in an analogous manner. Various kinds of restriction endonuclease can be used, if the digestion of the chromosomal DNA is done partially. Thereafter, the digested chromosomal DNA and vector DNA are subjected to a ligation reaction.

Recombination of DNA to prepare the recombinant plasmid can be carried out by incorporating terminal-transferase deoxyadenylic acid and thymidylic acid, or deoxyguanylic acid and deoxycytidylic acid into the chromosomal DNA fragment and cleaved vector DNA, and by subjecting the modified chromosomal DNA fragment and cleaved DNA to a ligation reaction.

As a suitable vector DNA, a conventional vector can be employed such as Col EI, pSC 101, pBR 322, R6K or phage, or their derivatives.

The hybrid DNA thus obtained can be incorporated into a microorganism of the genus Escherichia by conventional transformation techniques. The desired transformant is screened using a medium on which a clone, having one or both of the characteristics of phenylalanine productivity possessed by the chromosomal DNA fragment and those possessed by vector DNA, can only grow.

As the recipient microorganism for the hybrid DNA, any strain of the genus Escherichia can be used.

In order to increase productivity, the recipient microorganism desirably possesses the nutritional requirement of, for instance, tyrosine, tryptophan, isoleucine, methionine, histidine, arginine, proline, leucine, lysine, threonine, serine, adenine, guanine and xanthine, and resistance to, for instance, tyrosine-analogues, tryptophan-analogues, sulfa-drugs, singly or in combination. Preferably, the resistance or nutritional requirement is also possessed by the DNA donor.

The methods of culturing the L-phenylalanine producing strains thus obtained are conventional, and are similar to the methods for the cultivation of known L-phenylalanine producing microorganisms. Thus, the culture medium employed is a conventional one containing carbon sources, nitrogen sources, inorganic ions and, when required, minor organic nutrients such as vitamines or amino acids. Examples of suitable carbon sources include glucose, sucrose, lactose, starch hydrolysate and molasses. Gaseous ammonia, aqueous ammonia and ammonium salts and other nitrogen containing materials can be used as the nitrogen source. In the case where an organic acid such as fumaric acid, citric acid, acetic acid, gluconic acid, tartaric acid or malic acid is added to the medium, the yield of L-phenylalanine is usually improved.

Cultivation of the recombinant microorganisms is conducted under aerobic conditions in which the pH and the temperature of the medium are adjusted to a suitable level and continued until the formation of L-phenylalanine ceases.

The L-phenylalanine which accumlates in the culture medium can be recovered by a conventional procedure.

By the method of the present invention, L-phenylalanine can be produced in higher yields than has been achieved in previously known methods. Moreover, the amounts of by-product amino acids produced are very small, which, accordingly, greatly simplifies the recovery of L-phenylalanine in high yields.

Having generally discribed this invention, a further understanding can be obtained by reference to certain specific examples which are provided herein for purposes of illustration only and are not intended to be limiting unless otherwise specified.

EXAMPLE 1

(1) Preparation of chromosomal DNA possessing genetic information related to L-phenylalanine production.

*Escherichia coli* AJ 11380, a mutant resistant to p-fluorophenylalanine and induced from K-12 (ATCC 10798), was cultured at 37° C. for 3 hours with shaking in 1 l of L-medium containing 1 g/dl peptone, 0.5 g/dl yeast extract, 0.1 g/dl glucose and 0.5 g/dl NaCl (pH was adjusted to 7.2), and bacterial cells in the exponential growth phase were harvested. Chromosomal DNA was extracted by a conventional phenol-method, and 5.0 mg of purified DNA was obtained.

(2) Preparation of vector DNA

As the vector, the DNA of plasmid pBR 322, which contains both ampicillin and tetracycline resistant genes as makers, was prepared as follows:

A strain of *Escherichia coli* K-12 harboring the plasmid pBR 322 was incubated at 37° C. in 1 l of a glucose-"casamino acid"-inorganic salts medium, containing, 2 g glucose, 1 g $NH_4Cl$, 6 g $Na_2HPO_4$, 3 g $KH_2PO_4$, 5 g NaCl, 0.1 g $MgSO_4 \cdot 7H_2O$, 0.015 g $CaCl_2 \cdot 2H_2O$, 20 g "casamino acid", 0.05 g L-tryptophan, 0.05 g thymine and 100 µg thiamine·HCl, per liter (pH was adjusted to 7.2). After the strain was incubated until the late log phase, 170 µg/ml of chloramphenicol was added to the culture medium. Through this process, the plasmid DNA was amplified and accumulated abundantly in the bacterial cells.

After 16 hours of incubation, the cells were harvested and then lysed by treatment with lysozyme and SDS. The lysate was centrifuged at 30,000 Xg for 1 hour to obtain a supernatant. After concentrating the supernatant, 550 µg of the plasmid DNA was obtained by fractionation using cesium chloride-ethidium bromide equilibrium density gradient centrifugation.

(3) Insertion of chromosomal DNA fragment into vector.

Ten µg of the chromosomal DNA was treated with each of the restriction endonucleases EcoRI, Pst I, Hind III and Bam HI at 37° C. for 5, 10, 20, 30 and 60 minutes respectively, to cleave DNA chains, and then was heated at 65° C. for 5 minutes, respectively. Ten µg of the vector DNA was also treated with each of the restriction endonucleases, EcoRI, Pst I, Hind III and Bam HI at 37° C. for 1 hour to cleave the DNA completely, and then was heated at 65° C. for 5 minutes, respectively.

The digested chromosomal DNA solution and the cleaved vector DNA solution were mixed and subjected to the ligation reaction of DNA fragments by the $T_4$ phage DNA-ligase in the presence of ATP and dithiothreitol at 10° C. for 24 hours. The reaction mixture was then heated at 65° C. for 5 minutes, and two fold volumes of ethanol were added to it. The recombinant DNA which precipitated was recovered.

(4) Genetic transformation with the hybrid plasmid harboring the genetic information related to phenylalanine production.

An L-phenylalanine-requiring strain of *Escherichia coli* No. 123, which was derived from *Escherichia coli* K-12 by N-methyl-N'-nitro-N-nitrosoguanidine mutagenesis, was cultured in 10 ml of L-medium at 37° C. with shaking. Cells in the exponential growth phase were harvested, and suspended in a 0.1 M $MgCl_2$ solution and then in a 0.1 M $CaCl_2$ solution in an ice-bath, whereby, +competent" cells having the ability of DNA uptake were prepared.

Into the competent cell suspension, the DNA obtained in step (3), which contains the hybrid plasmid DNA, was added. The suspension was kept in an ice-bath for 30 minutes, then heated at 42° C. for 2 minutes, and again allowed to stand in an ice-bath for 30 minutes. The cells, thus containing the hybrid plasmid DNA, were inoculated into an L-medium and the medium was shaken at 37° C. for 3 hours, whereby the transformation reaction was completed. The cells were harvested, washed, and resuspended. A small portion of the cell suspension was spread on an agar plate containing, 2 g glucose, 1 g $(NH_4)_2SO_4$, 7 g $K_2HPO_4$, 2 g $KH_2PO_4$, 0.1 g $MgSO_4 \cdot 7H_2O$, 0.5 g sodium citrate·$2H_2O$ and 2 g agar, per liter, (pH was adjusted to 7.2). The plate was incubated at 37° C. After 3 days incubation, all of the colonies which appeared were picked up, purified and isolated.

Colonies, which were resistant to at least one of the antibiotics, ampicillin and tetracycline and which had the ability of producing phenylalanine were obtained as the transformant. Resistance to ampicillin (50 µg/ml) and to tetracycline (5 µg/ml) was tested using an agar-L-medium, and L-phenylalanine productivity was examined by the formation of a halo on a minimum-agar-medium on which phenylalanine requiring mutant No. 123 had previously been spread.

(5) Production of L-phenylalanine by the prepared phenylalanine-producing strain.

Table 1 shows the experimental result of the fermentative production of L-phenylalanine using strain AJ 11379 (NRRL B-12117), which is one of the clones obtained in step (4). This strain was sent by registered mail to FERMENTATION RESEARCH INSTITUTE, AGENCY OF INDUSTRIAL SCIENCE AND TECHNOLOGY on June 15, 1979 and has registration number 104 wo (Japanese letter "ア") a 137, and assigned the accession number: FERM-P 5043.

The fermentation medium contained 5 g/dl glucose, 2.5 g/dl ammonium sulfate, 0.2 g $KH_2PO_4$, 0.1 g/dl $MgSO_4 \cdot 7H_2O$, 0.1 g/dl yeast extract, 1000 µg/l thiamine·HCl, 1 mg/dl $FeSO_4 \cdot 7H_2O$, 1 mg/dl $MnSO_4 \cdot 4H_2O$ and 2.5 g/dl $CaCO_3$ (separately sterilized) and the pH was adjusted to 7.0.

Twenty ml of the fermentation medium was placed in a 500 ml flask, inoculated with one loopful inoculum of the test microorganism, and the cultivation was performed at 31° C. for 72 hours.

The amount of L-phenylalanine in the supernatant of the fermentation broth was determined by microbiological assay.

TABLE 1

| Microorganism tested | Amount of L-phenylalanine accumulated (mg/dl) |
|---|---|
| *Escherichia coli* AJ 11380 | 30 |

TABLE 1-continued

| Microorganism tested | Amount of L-phenylalanine accumulated (mg/dl) |
|---|---|
| *Escherichia coli* AJ 11379 | 120 |

(6) Incorporation of the hybrid plasmid into L-phenylalanine non-requiring strains.

The hybrid plasmid contained in AJ 11379 was isolated by the method similar to that shown in step (2), and incorporated into *Escherichia coli* K-12 (ATCC 10798), *Escherichia coli* No. 22 (L-tyrosine requiring strain derived from K-12), *Escherichia coli* No. 176 (p-fluorophenylalanine resistant strain derived from K-12) and *Escherichia coli* No. 67 (L-tyrosine requiring and p-fluorophenylalanine resistant strain derived from K-12).

The transformants, AJ 11569 (NRRL B-12144) AJ 11570 (NRRL B-12145), AJ 11571 (NRRL B-12146) and AJ 11572 (NRRL B-12147), selected as ampicillin and tetracycline resistant colonies, were subjected to the fermentative production of L-phenylalanine by a method similar to that described in step (5) except that 10 mg/dl of L-tyrosine was added to the fermentation medium for strains No. 22, AJ 11570, No. 67 and AJ 11572.

The amount of L-phenylalanine produced was determined by microbiological assay. The results are shown in Table 2.

TABLE 2

| Strain | recipient or transformant | marker | L-phenylalanine (g/l) |
|---|---|---|---|
| K-12 | recipient | (wildtype) | 0.00 |
| AJ 11569 | transformant | AMP$^{r*1}$, TC$^{r*2}$, PFP$^{r*3}$ | 1.16 |
| No. 22 | recipient | Tyr$^-$ | 0.36 |
| AJ 11570 | transformant | Tyr$^-$, Amp$^r$, TC$^r$, PFP$^r$ | 2.80 |
| No. 176 | recipient | PFP$^r$ | 0.40 |
| AJ 11571 | transformant | PFP$^r$, Amp$^r$, TC$^r$ | 1.30 |
| No. 67 | recipient | Tyr$^-$, PFP$^r$ | 2.00 |
| AJ 11572 | transformant | Tyr$^-$, PFP$^r$, Amp$^r$, TC$^r$ | 3.90 |

*[1] resistant to ampicillin
*[2] resistant to tetracyclin
*[3] resistant tp p-fluorophenylalanine

Having now fully described the invention, it will be apparent to one of ordinary skill in the art that many changes and modifications can be made thereto without departing from the spirit or scope of the invention as set forth herein.

What is claimed

1. A method for producing L-phenylalanine by fermentation, which comprises:
   culturing in a culture medium an L-phenylalanine producing microorganism selected from the group consisting of *Escherichia coli* NRRL B-12141, *Escherichia coli* NRRL B-12145, *Escherichia coli* NRRL B-12146 and *Escherichia coli* NRRL B-12147 constructed by incorporating a hybrid plasmid in a recipient strain of the genus Escherichia and recovering the L-phenylalanine which accumulates in the culture medium, said hybrid plasmid containing a deoxyribonucleic acid fragment possessing genetic information related to L-phenylalanine production and obtained from a phenylalanine analogue resistant mutant of the genus Escherichia.

2. The method of claim 1, wherein said culture medium contains carbon sources, nitrogen sources, inorganic ions and other nutrients.

3. The method of claim 2, wherein said carbon source is sucrose, glucose, lactose, starch hydrolysate or molasses.

4. The method of claim 2, wherein said nitrogen source is ammonia or an ammonium salt.

5. The method of claim 1, wherein said Escherichia mutant is resistant to o-, m- or p-fluorophenylalanine; o-, m- or p-aminophenylalanine; β-phenylserine, cyclohexylalanine; α-amino-β-phenylethane sulfonic acid; o-, m- or p-chlorophenylalanine; o-, m- or p-bromophenylalanine; β-2-thienylalanine; β-3-thienylalanine; β-2-furylalanine; β-2-pyrolealanine; 1-cyclopentene-1-alanine; 1-cyclohexan-1-alanine; 2-amino-4-methyl-4-hexenic acid; S-(1,2-dichlorovinyl)-cysteine; β-4-pyridylalanine; β-2-pyridylalanine, β-4-pyrazolealanine or p-nitrophenylalanine.

* * * * *